United States Patent [19]

Goddard

[11] 3,933,927

[45] Jan. 20, 1976

[54] PHENOL TRANSALKYLATION PROCESS
[75] Inventor: Lloyd E. Goddard, Orangeburg, S.C.
[73] Assignee: Ethyl Corporation, Richmond, Va.
[22] Filed: Apr. 13, 1973
[21] Appl. No.: 351,015

Related U.S. Application Data
[63] Continuation-in-part of Ser. No. 20,115, March 16, 1970, abandoned.

[52] U.S. Cl............................ 260/624 E; 260/621 E
[51] Int. Cl.² .......................................... C07C 39/06
[58] Field of Search ........ 260/624 R, 624 C, 624 E, 260/621 E, 613

[56] References Cited
UNITED STATES PATENTS

| | | | |
|---|---|---|---|
| 2,831,898 | 4/1958 | Ecke et al. | 260/624 E |
| 3,075,832 | 1/1963 | Ecke et al. | 260/624 E |
| 3,091,646 | 5/1963 | Leston | 260/624 R |
| 3,534,111 | 10/1970 | Hess | 260/624 E |

*Primary Examiner*—James O. Thomas, Jr.
*Assistant Examiner*—W. B. Lone
*Attorney, Agent, or Firm*—Donald L. Johnson; Robert A. Linn; Joseph D. Odenweller

[57] ABSTRACT

Phenols having an unsubstituted ortho position are transalkylated in the ortho position by mixing them with an ortho-alpha-branched alkylphenol (e.g., 2,6-di-sec-butylphenol) and an aluminum phenoxide catalyst and heating the mixture to 100°–350°C., preferably in a closed system and in the presence of olefin corresponding in structure to the ortho-alpha-branched alkyl group.

2 Claims, No Drawings

PHENOL TRANSALKYLATION PROCESS

This application is continuation-in-part of application Ser. No. 20,115, filed Mar. 16, 1970.

BACKGROUND

A number of methods are available to alkylate phenols with alpha-branched alkyl groups. For example, the reaction of an olefin, such as propylene, isobutylene or butene, with phenol in the presence of an acid catalyst leads to a mixture of alpha-branched alkylphenols. In another method, described in U.S. Pat. No. 2,831,898, an aluminum phenoxide catalyst is employed which leads to selective orthoalkylation of the phenol. In either case, it frequently occurs that some of the coponents in the product mixture contain more alkyl groups than desired or have the alkyl groups substituted in the wrong position. For example, in the alkylation of phenol with butene using an aluminum phenoxide catalyst the product in greatest demand is generally o-sec-butyl-phenol. This is an intermediate in the production of 2,4-di-nitro-6-sec-butylphenol, a valuable selective herbicide. In the aluminum phenoxide catalyzed alkylation of phenol to prepare o-sec-butylphenol some polyalkylation occurs leading to, for example, 2,6-di-sec-butylphenol. In the past, unless some market could be found, the 2,6-di-sec-butylphenol was either discarded or, at best, subjected to a separate dealkylation process such as described by Kolka et al., J. Org. Chem., 22, 1957, or in British Pat. No. 940,378. The Kolka et al. dealkylation process is shown to be applicable to ortho-tert-butylphenol and the British Pat. No. 940,378 dealkylation process is said to be applicable to para alkylphenols. These methods of recovering phenol valve not only require a separate process step but also result in loss of dealkylated olefin.

Other related processes which are acknowledged are U.S. Pat. No. 3,418,380 disclosing transalkylation of tert-butyl groups employing a sulfuric acid catalyst. Dealkylation of 4,6-di-tert-alkyl-m-cresol using an aluminum phenoxide catalyst is disclosed in U.S. Pat. No. 3,091,646. Transalkylation of p-cresol by 2,6-di-tert-butyl-p-cresol using a polystyrene sulfonic acid catalyst is disclosed in U.S. Pat. No. 2,802,884. Other pertinent prior art is U.S. Pat. No. 2,578,597; U.S. Pat. No. 3,417,149; U.S. Pat No. 3,519,692; British Pat. No. 776,204 and British Pat. No. 1,062,298. Accordingly, a need exists for a process that can convert di-ortho-sec-alkylated phenols co-produced in alkylation processes to lower alkylated phenols and, at the same time, transfer the ortho-sec-alkyl group removed from the di-alkylated phenol to another phenolic compound to yield a more desirable product.

SUMMARY

According to the present invention, there is provided a process for transalkylating a phenol having an open ortho position by mixing this recipient phenol with an alpha-branched alkylphenol having at least one, and preferably two, alpha-branched alkyl groups in an ortho position, and then heating this mixture to about 100°–350°C. in the presence of an aluminum phenoxide catalyst.

DESCRIPTION OF THE PREFERRED EMBODIMENTS

A preferred embodiment of this invention is a process for transalkylating a phenol in a position ortho to a phenolic hydroxyl group, said phenol having at least one position on its phenolic benzene ring ortho to said phenolic hydroxyl group unsubstituted except for hydrogen, said process comprising mixing said phenol with an alpha-branched alkylphenol in which at least one alpha-branched alkyl group is bonded to the phenolic benzene ring of said alpha-branched alkylphenol ortho to its phenolic hydroxyl group and a catalytic amount of an aluminum phenoxide and heating the mixture to a temperature of from about 100°–350°C. In a simple form the transalkylation can be shown as follows:

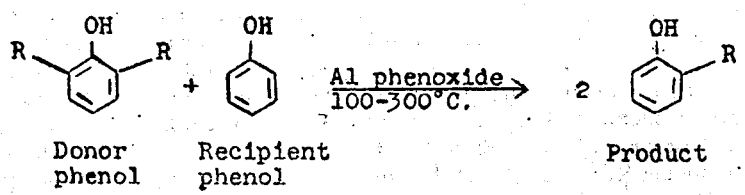

Donor phenol    Recipient phenol    Product

The phenol having an unsubstituted ortho position is referred to as the recipient phenol and is a phenol in which at least one position on the phenolic benzene ring ortho to the phenolic hydroxyl group is unsubstituted except for hydrogen. Some examples of these are:

o-cresol
2,4-xylenol
4-tert-butylphenol
2-n-eicosylphenol
p-phenylphenol
2-n-octyl-p-cresol
4-chloro-o-cresol
α-naphthol
o-isopropylphenol
2,4-di-sec-butylphenol
β-naphthol
2,4-dinitrophenol
2,4-dibromophenol
p-methoxy-o-cresol
o-eicosyloxyphenol The benefits of the process are most appreciated when the recipient phenol has both an unsubstituted ortho and para position because, under these circumstances, the process not only transalkylates but does so selectively in an ortho position. In the past, similar processes conducted on ortho-para unsubstituted phenols employing other catalysts such as sulfuric acid or Friedel-crafts catalysts have not resulted in selective ortho transalkylation, but rather, have given a mixture of products. Some examples of the preferred recipient phenols are as follows:

o-cresol
o-chlorophenol
o-bromophenol
o-nitrophenol o-methoxyphenol
o-phenylphenol
o-n-butylphenol
o-isooctylphenol
o-n-eicosylphenol
o-isopropylphenol
o-sec-amylphenol
and the like The most preferred recipient phenol is the compound phenol $C_6H_5OH$.

The donor phenol is an ortho-alpha-branched alkylphenol which may be substituted in the remaining nuclear position with other groups. These can be illustrated by the formula:

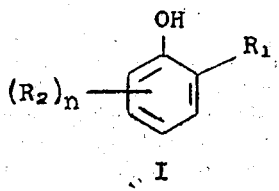

in which $R_1$ is an alpha-branched alkyl group containing from 3 to about 50 carbon atoms, $n$ is an integer from 0-4, and $R_2$ can be a $C_{1-20}$ aklyl, $C_{6-20}$ cycloalkyl, $C_{6-20}$ aryl, $C_{7-20}$ aralkyl, or a non-hydrocarbon group such as a halogen, nitro, $C_{1-20}$ alkoxy, or any other radical which does not interfere with the course of the reaction. The migrating or transalkylating group in the donor phenol of Formula I is represented by $R_1$, the alpha-branched alkyl group. In a highly preferred embodiment $R_1$ is a $C_{3-50}$-sec-alkyl group.

The donor phenol is preferably a polysubstituted phenol. The reason that the process is generally carried out with at least one substituuent other than $R_1$, represented by $R_2$ in Formula I, is not that the process won't operate without the further substituents but, rather, that there is generally no practical reason to carry out the process when the donor phenol has but a single substituent. For example, if the recipient phenol was phenol itself and the donor phenol was o-sec-butylphenol (a donor phenol unsubstituted except for the single ortho-alpha-branched alkyl group) then, even after the alpha-branched alkyl group ortho-transalkylated the recipient phenol, the final state would be the same as the initial state because the donor phenol would be converted to phenol. However, there may exist circumstances when a simple mono-substituted ortho-alpha-branched alkylphenol might be desired as the donor phenol. This could occur when the recipient phenol is a compound other than phenol itself.

Some examples of useful donor phenols are:
2-tert-butyl-p-cresol
2,4-diisopropylphenol
o-sec-butylphenol
o-tert-butylphenol
2,6-dicyclohexylphenol
2,6-di-sec-butyl-p-nitrophenol
2,4-di-tert-eicosylphenol
2,4-di(α-methylbenzyl)phenol
o-(α,α-dimethylbenzyl)phenol
2,4-di-tert-butylphenol
2,4,6-tri-sec-butylphenol
2-tert-eicosylphenol
2,4-di-sec-triacontylphenol
2-sec-tetracontylphenol
2-sec-pentacontylphenol
2,4,6-tri-tert-butylphenol
2-tert-butyl-4-methoxyphenol
2-sec-butyl-4-isopropoxyphenol
2-tert-octyl-4-eicosyloxyphenol
2,4-dichloro-6-tert-butylphenol
2-tert-butyl-4-chlorophenol
2-tert-butyl-6-bromophenol
2,6-diisopropyl-p-cresol
2,6-di-tert-butyl-p-nitrophenol
2-tert-amyl-p-phenylphenol Of the above, the preferred are the hydrocarbon-substituted phenols.

A more preferred donor phenol is one in which there are at least two alpha-branched alkyl groups substituted in the phenol ring, at least one of which is ortho to the phenolic hydroxyl. In other words, at least one $R_2$ in Formula I is an alpha-branched alkyl group containing about 3-20 carbon atoms and $n$ is at least 1. Some examples of these preferred donor phenols are:
2,4-di-tert-butylphenol
2,4,6-tri-tert-butylphenol
2,4-di-sec-butylphenol
2,4,6-tri-sec-butylphenol
2,4-dicyclohexylphenol
2,6-di-tert-octylphenol
2,6-di-tert-butyl-p-cresol
2,6-di-sec-butyl-p-chlorophenol
2,4-di-tert-butyl-p-methoxyphenol
2,4-di-sec-dodecylphenol
2,4-di-sec-eicosylphenol A more preferred donor phenol is one having both positions ortho to the phenolic hydroxyl substituted with an alpha-branched alkyl group. Some examples of these are:
2,6-di-tert-butyl-p-cresol
2,4-di-tert-butyl-6-sec-butylphenol
2,6-di-sec-butyl-p-chlorophenol
2,6-diisopropyl-p-nitrophenol
2,4,6-tri-tert-octylphenol
2,6-di-tert-eicosyl-p-cresol In the most preferred case the donor phenol is a 2,6-di-sec-alkylphenol. Some examples of this class of donor phenol are:
2,6-di-sec-pentylphenol
2,6-diisopropylphenol
2,6-di-sec-butylphenol
2,6-dicyclohexylphenol
2,6-di-sec-octylphenol
2,6-di-sec-dodecylphenol
2,6-di-sec-eicosylphenol
2,6-di-sec-triacontylphenol
2,6-di-sec-tetracontylphenol
2,6-di-sec-pentacontylphenol
2-isopropyl-6-sec-butylphenol In a most highly preferred embodiment the donor phenol is 2,6-di-sec-butylphenol and the recipient phenol is phenol itself. A very useful form of the 2,6-di-sec-butylphenol is as a mixture consisting essentially of about 0–15 weight percent o-sec-butylphenol, 50–90 weight percent 2,6-di-sec-butylphenol, 0–15 weight percent p-sec-butylphenol, 1–15 weight percent 2,4-di-sec-butylphenol and 0–5 weight percent 2,4,6-tri-sec-butylphenol obtained by distilling phenol and o-sec-butylphenol from the reaction product obtained by reacting phenol with butene in the presence of an aluminum phenoxide catalyst at a temperature of from about 100°–500°C., preferably from 200°–300°C., in the manner described in U.S. Pat. No. 2,831,898.

In general, from about 0.001 to 10 moles of donor phenol can be uitlized per mole of recipient phenol. Preferably, the recipient phenol is in molar excess. In other words, a more preferred range is from about 0.001 to 1 mole of donor phenol per mole of recipient phenol.

The aluminum phenoxide catalyst is a compound having at least one phenoxide group bonded to an aluminum atom. The phenoxide radical may be derived from phenol or any of the donor or recipient phenols. For example, if the recipient phenol is paracreasol the aluminum phenoxide can be aluminum tris (p-methylphenoxide). Likewise, the aluminum phenoxide may correspond to the donor phenol. Frequently, because of the manner in which it is made, it is a mixture derived from both donor and recipient phenol. Furthermore, as the transalkylation proceeds, the nature of the aluminum phenoxide, being in dynamic equilibrium with the composition of the mixture, changes. This does not affect the operability of the process and is inherent in the process.

The aluminum phenoxide can be made by a variety of methods. For example, aluminum metal, either granular or ribbon, can be heated with a phenol to about 150°–200°C., causing the aluminum to react with evolution of hydrogen, forming an aluminum phenoxide. A small amount of mercuric chloride catalyzes this reaction. If desired, an aluminum alkyl such as triethyl aluminum can be added to the phenol, forming an aluminum phenoxide.

Generally, the aluminum phenoxide is an aluminum tris phenoxide, but this is not required. For example, the aluminum phenoxide can be made by adding aluminum chloride to the phenol and venting evolved hydrogen chloride, forming an aluminum phenoxide having the empirical formula: diphenoxy aluminum chloride. Likewise, small amounts of water in the phenol result in the formation of a phenoxy aluminum hydroxide such as diphenoxy aluminum hydroxide, which is also an active catalyst.

The amount of aluminum phenoxide should be sufficient to cause the transalkylation to proceed at a reasonable rate. Good results are achieved when from about 0.01 to 0.1 mole parts of aluminum are present as an aluminum phenoxide for each mole part of phenol (both donor and recipient). A preferred catalyst concentration range is from about 0.02 to 0.04 mole parts of aluminum as an aluminum phenoxide per mole part of phenol.

The transalkylation can be conducted in a temperature range of from about 100°–350°C. When the transalkylating group is a tertiary alkyl radical the preferred temperature range is from about 100°–200°C., especially around 110°–150°C. When the transalkylating radical is a secondary alkyl group the preferred temperature range is from about 200°–350°C., especially about 225°–275°C.

The process is best carried out in a substantially closed system to prevent olefin and phenol from escaping and to give a higher transalkylation yield. When carried out in this manner, the donor and recipient phenol plus the catalyst can be merely mixed and heated in the closed system, allowing the pressure to seek its level under the particular conditions. In a more preferred embodiment from about 0.1–100 moles per mole of donor and recipient phenol of olefin corresponding in structure to the transalkylating alkyl group ($R_1$ in Formula I) is added to further minimize the amount of escaping olefin. By corresponding in structure is meant having the same structure that the migrating alkyl would have if removed from the donor phenol and an olefinic double bond placed between the carbon atom formerly bonded to the phenol ring and an adjoining carbon atom. A few examples of representative alkyls and corresponding olefins are as follows: isopropyl-propylene; sec-butyl-butene-1 or -2; tert-butyl-isobutylene.

The pressure in the closed system depends on the temperature and vapor pressure of the reactants, especially the olefin. A useful range to be anticipated is from 50 to about 1000 psig.

An especially facile method to carry out the process is to mix the donor and recipient phenols and the catalyst (or, alternatively, to form the catalyst in situ by adding aluminum or an aluminum alkyl and heating) and then heating the mixture in a closed system until the transalkylation has proceeded to a substantial degree and then adding olefin corresponding in structure to the desired alkyl group and continuing the alkylation in the manner prescribed in U.S. Pat. No. 2,831,898 until the yield of desired product is optimized.

The manner in which the process is carried out is illustrated by the following examples. All parts are by weight unless otherwise specified.

EXAMPLE 1

In a pressure reaction vessel equipped with stirrer and heating means was placed 188 parts of phenol and 6.4 parts of granular aluminum. The vessel was flushed with nitrogen, sealed and heated. At 182°C., a reaction initiated, causing the temperature to rise sharply to 262°C. This was the reaction of the aluminum with the phenol to form the aluminum phenoxide catalyst. The vessel was then cooled and evolved hydrogen vented. Then, 356.4 parts of 2,6-diisopropylphenol were added and the vessel again sealed and heated to 250°C. The mixture was stirred at this temperature for 11 hours and then cooled and hydrolyzed with dilute hydrochloric acid. The product was washed with water until neutral and analyzed by vapor phase chromatography. The results showed that phenol had been consumed with the formation of 106.5 parts of o-isopropylphenol.

EXAMPLE 2

In the reaction vessel of Example 1 place 190 parts of phenol and 2.4 parts of granular aluminum. Flush with nitrogen and heat to 180°C. to form aluminum phenoxide. Cool and vent. Add 206 parts of 2,6-di-sec-butylphenol and again seal the vessel. Heat to 275°C. and stir at this temperature for 2 hours. Then pressurized with butene-1 to 1000 psig and stir the reaction mixture under these conditions for an additional 4 hours. Cool and discharge the reaction mixture into a dilute aqueous hydrochloric acid solution to hydrolyze the catalyst. Wash with water until neutral and then distill the reaction mixture to recover o-sec-butylphenol. Residual 2,6-di-sec-butylphenol remaining is recycled to a subsequent reaction carried out in the same manner as the foregoing. The net result is that the 2,6-di-sec-butylphenol formed in each reaction is consumed in a subsequent reaction as the donor phenol forming o-sec-butylphenol, thus, avoiding accumulation of 2,6-di-sec-butylphenol and giving higher yields of o-sec-butylphenol.

EXAMPLE 3

In the reaction vessel of Example 1 place 1 mole part of p-cresol and 0.025 moles of aluminum turnings. Heat to 185°C. to form an aluminum phenoxide catalyst. Cool, vent hydrogen, and add 5 moles of 2,4,6-tri-tert-butylphenol. Heat to 130°C. and stir for 4 hours. Cool to 100°C., vent, and hydrolyze with dilute hydrochloric acid. Distill recover from the reaction product a mixture of 2-tert-butyl-p-cresol and 2,6-di-tert-butyl-p-cresol, a useful antioxidant.

EXAMPLE 4

In the reaction vessel of Example 1 place 1 mole part of phenol and 0.05 moles of aluminum chloride. Heat to 120°C. and vent. Pass nitrogen through the mixture at this temperature to remove residual hydrogen chloride. Continue this until about two-thirds of the chlorine added as aluminum chloride has been removed. The catalyst at this point corresponds to the composition diphenoxy aluminum chloride. Cool and add 5 mole parts 2,4,6-tri-tert-butylphenol, seal and heat to 125°–13°C. and hold at this temperature while stirring for 4 hours. Following this, cool to below 100°C., vent and hydrolyze the mixture with dilute hydrochloric acid, wash with water until neutral, and distill to recover from the mixture o-tert-butylphenol and 2,6-di-tert-butylphenol, both valuable antioxidants.

EXAMPLE 5

In a pressure vessel of Example 1 place 1 mole of phenol and 0.03 moles of aluminum. Seal and heat to 190°C. to form the aluminum phenoxide catalyst. Cool to 100°C. and vent hydrogen, seal and heat to 240°C. and pressurize to 1000 psig with butene-1. Hold 4 hours while stirring at 230°–250°C. and then cool to below 100°C., vent, and hydrolyze the reaction mixture. Wash with water until neutral and then distill the mixture to recover the principal product, o-sec-butylphenol. The distillation bottoms contain a mixture consisting mainly of about 80 percent 2,6-di-sec-butylphenol, 8 percent 2,4-di-sec-butylphenol, 6 percent 4-sec-butylphenol, 2 percent 2-sec-butylphenol, and 4 percent 2,4,6-tri-sec-butylphenol. Transfer these bottoms to a second pressure reaction vessel containing one mole part of phenol. Then add 0.3 moles of aluminum and heat to 200°C. to form an aluminum phenoxide catalyst. Cool to 100°C. and vent. Seal and heat to 275°C. and stir at this temperature for one hour. The pressurize to 500 psig with butene-1 and stir an additional 4 hours at 250°–275°C. Cool the mixture and vent residual pressure. Hydrolyze the product and wash with water until neutral. Distill the resultant misture to recover, as the principal product, o-sec-butylphenol, and then recycle the bottoms to a subsequent transalkylation-alkylation process carried out in the same manner as above.

EXAMPLE 6

In a pressure reaction vessel place one mole of p-chlorophenol and 0.02 moles of triethyl aluminum. Stir and heat to 100°C. Cool, vent, and then add one mole of 2,4-di-tert-butylphenol. Seal and heat to 125°C. and stir at 125°–135°C. for 2 hours. Cool, hydrolyze with dilute hydrochloric acid and wash with water. Distill to recover a substantial portion of 2-tert-butyl-p-chlorophenol, a useful bactericide.

EXAMPLE 7

In a pressure reaction vessel of Example 1 place one mole of phenol and 0.1 mole of aluminum. Seal and heat to 200°C. to form an aluminum phenoxide catalyst. Cool to below 100°C., vent, and add two moles of 2,4,6-tri($\alpha$-methylbenzyl)phenol. Reseal and heat to 150°C. Stir at 130–150°C. for one hour and then cool to below 100°C. and discharge the mixture into dilute hydrochloric acid. Wash the product until neutral and distill under vacuum to recover both o-($\alpha$-methylbenzyl)phenol and 2,6-di-($\alpha$-methylbenzyl)phenol.

EXAMPLE 8

In a pressure reaction vessel as in Example 1 place 1 mole of phenol and 0.15 moles of diethyl aluminum chloride. Then add 2 moles of 2,4-dicyclohexylphenol, seal the vessel, and heat to 150°C. Stir at this temperature for 3 hours and then cool. Hydrolyze with dilute hydrochloric acid and recover by distillation, as the principal product, o-cyclohexylphenol.

EXAMPLE 9

In a pressure reaction vessel as in Example 1 place 1 mole of p-methoxyphenol. Add 0.2 moles of triethyl aluminum and heat to 50°C., allowing ethane to evolve. Then add 5 moles of 2,4,6-tri-tert-butylphenol and seal. Heat to 130°C. and stir at this temperature for 4 hours. Cool to below 100°C. and hydrolyze. Distill the mixture to recover 2-tert-butyl-4-methoxyphenol and 2,6-di-tert-butyl-4-methoxyphenol, both valuable antioxidants useful in food and animal feed.

EXAMPLE 10

Into an autoclave is placed 19,650 parts of phenol and 43,350 parts of a mixture containing 2 weight percent o-sec-butylphenol, 69 weight percent 2,6-di-sec-butylphenol, 4 weight percent 4-sec-butylphenol, 9 weight percent 2,4-di-sec-butylphenol and 7 weight percent 2,4,6-tri-sec-butylphenol. This mixture is obtained by alkylating phenol with n-butene using an aluminum phenoxide catalyst and distilling out unreacted phenol and o-sec-butylphenol (as described in U.S. Pat. No. 2,831,898, incorporated herein by reference). The aluminum phenoxide used to catalyze the alkylation is not removed from the resultant distillation bottoms. The autoclave is sealed and heated to 280°C. and maintained at this temperature for six hours. At the end of this time it is cooled and discharged. The product is then distilled to recover 15,000 parts of o-sec-butylphenol.

From the foregoing, the manner in which the process is carried out is clear. The procedures can readily be extended to other donor and recipient phenols by substituting these in the above examples as previously described.

The phenols made by this invention are useful for a number of purposes such as antioxidants and bactericides. One especially useful phenol is o-sec-butylphenol, made by transalkylating phenol with 2,6-di-sec-butylphenol, 2,4-di-sec-butylphenol, 2,4,6-tri-sec-butylphenol, or mixtures of these. This compound may be readily converted to 2,4-dinitro-6-sec-butylphenol following the general procedure described in U.S. Pat. No. 2,810,767. The nitrated product is a very useful herbicide.

I claim:

1. A process for selectively ortho-transalkylating phenol, said process comprising mixing said phenol with 2,6-di-sec-butylphenol and about 0.01 to 0.1 mole parts per mole part of phenol and 2,6-di-sec-butylphenol of an aluminum phenoxide and heating the mixture in a closed system to a temperature of about 100°–350°C whereby a sec.-butyl group from the 2,6-di-sec-butyl phenol is thereby transferred selectively to an ortho position of the phenol.

2. A process of claim 1 carried out in the presence of added butene.

* * * * *